(12) United States Patent
Baek

(10) Patent No.: US 12,064,503 B2
(45) Date of Patent: Aug. 20, 2024

(54) HIGH-POTENCY VITAMIN C AND SUGAR ALCOHOL TOPICAL FORMULATIONS

(71) Applicant: ICB (an ABC), LLC, San Jose, CA (US)

(72) Inventor: Jihoon P. Baek, Los Angeles, CA (US)

(73) Assignee: ICB (an ABC) LLC, Los Angeles, CA (US)

( * ) Notice: Subject to any disclaimer, the term of this patent is extended or adjusted under 35 U.S.C. 154(b) by 0 days.

(21) Appl. No.: 17/965,628

(22) Filed: Oct. 13, 2022

(65) Prior Publication Data

US 2023/0049595 A1    Feb. 16, 2023

Related U.S. Application Data

(63) Continuation of application No. PCT/US2021/027827, filed on Apr. 16, 2021.

(60) Provisional application No. 63/010,884, filed on Apr. 16, 2020.

(51) Int. Cl.

| A61K 8/67 | (2006.01) |
|---|---|
| A61K 8/34 | (2006.01) |
| A61K 8/42 | (2006.01) |
| A61K 8/92 | (2006.01) |

(52) U.S. Cl.
CPC ............ *A61K 8/676* (2013.01); *A61K 8/345* (2013.01); *A61K 8/42* (2013.01); *A61K 8/92* (2013.01)

(58) Field of Classification Search
None
See application file for complete search history.

(56) References Cited

U.S. PATENT DOCUMENTS

| 2,539,483 | A | 1/1951 | Ruskin |
|---|---|---|---|
| 4,960,764 | A | 10/1990 | Figueroa et al. |
| 4,983,382 | A | 1/1991 | Wilmott et al. |
| 5,140,043 | A | 8/1992 | Darr et al. |
| 5,308,621 | A | 5/1994 | Taylor et al. |
| 5,670,139 | A | 9/1997 | Allard et al. |
| 5,736,567 | A | 4/1998 | Cantin et al. |
| 5,925,679 | A | 7/1999 | Mather et al. |
| 6,013,255 | A | 1/2000 | Edens et al. |
| 6,020,367 | A | 2/2000 | Duffy et al. |
| 6,146,664 | A | 11/2000 | Siddiqui |
| 6,361,783 | B2 | 3/2002 | Moaddel et al. |
| 6,462,025 | B2 | 10/2002 | Vishnupad |
| 7,108,860 | B2 | 9/2006 | Dueva et al. |
| 7,179,841 | B2 | 2/2007 | Zielinski et al. |
| 8,313,756 | B1 | 11/2012 | Landau et al. |
| 8,344,024 | B2 | 1/2013 | Czarnota et al. |
| 9,018,177 | B2 | 4/2015 | Lauten et al. |
| 9,132,080 | B2 | 9/2015 | Zecchino et al. |
| 9,248,082 | B2 | 2/2016 | Pinnell et al. |
| 9,901,533 | B2 | 2/2018 | Zecchino et al. |
| 10,435,536 | B2 | 10/2019 | Swanzy |
| 10,532,017 | B2 | 1/2020 | Lema et al. |
| 2001/0007653 | A1 | 7/2001 | Moaddel et al. |
| 2004/0033963 | A1 | 2/2004 | Yu et al. |
| 2004/0067890 | A1 | 4/2004 | Gupta |
| 2004/0219122 | A1 | 11/2004 | Masuda et al. |
| 2005/0008592 | A1 | 1/2005 | Gardel et al. |
| 2005/0154054 | A1 | 7/2005 | Zielinski et al. |
| 2007/0077261 | A1 | 4/2007 | Zhang |
| 2007/0172436 | A1 | 7/2007 | Zhang |
| 2008/0057014 | A1 | 3/2008 | Masuda et al. |
| 2008/0175919 | A1 | 7/2008 | Mohammadi et al. |
| 2009/0312724 | A1* | 12/2009 | Pipkin ............... A61K 31/724 128/207.18 |
| 2013/0131162 | A1 | 5/2013 | Kaplan |
| 2014/0142175 | A1 | 5/2014 | Kelada et al. |
| 2014/0147525 | A1 | 5/2014 | de Paula et al. |
| 2015/0250709 | A1 | 9/2015 | Gan et al. |
| 2016/0101029 | A1 | 4/2016 | Sanmiguel |
| 2016/0256369 | A1 | 9/2016 | Dutton et al. |
| 2016/0354328 | A1* | 12/2016 | Huang ............... A61K 9/2054 |
| 2017/0224760 | A1 | 8/2017 | Garruto et al. |
| 2018/0071203 | A1 | 3/2018 | Gan et al. |
| 2018/0116927 | A1 | 5/2018 | Chaudhuri |
| 2018/0228714 | A1* | 8/2018 | Thomas ............... A61Q 19/08 |

(Continued)

FOREIGN PATENT DOCUMENTS

| CN | 1192134 A | 9/1998 |
|---|---|---|
| CN | 101282708 A | 10/2008 |

(Continued)

OTHER PUBLICATIONS

Belcher, L. A. et al. "Evaluating 1,3-Propanediol for Potential Skin Effects." Cosmetics & Toiletries, vol. 125, No. 5, May 2010, pp. 1-4.

Choi, Y.K. et al., "Effects of vitamin C vs. multivitamin on melanogenesis: comparative study in vitro and in vivo," International journal of Dermatology, vol. 49, Iss. 2, Feb. 2010, pp. 218-226.

Espinal-Perez, L.E. et al., "A double-blind randomized trial of 5% ascorbic acid vs. 4% hydroquinone in melasma," International Journal of Dermatology 43(8), Aug. 2004, pp. 604-607.

(Continued)

*Primary Examiner* — Jennifer A Berrios
(74) *Attorney, Agent, or Firm* — Fenwick & West LLP

(57) ABSTRACT

Topical formulations of L-ascorbic acid dissolved in a combination of a sugar alcohol agent, and a non-aqueous skin-compatible solvent are provided. The formulations are storage stable for an extended period of time without significant degradation of the L-ascorbic acid in the composition, and have desirable physical properties. The topical formulations can include high concentrations of the L-ascorbic acid. Topical compositions of this disclosure find use in treating or preventing a variety of cosmetic and/or dermatological conditions as well as to reduce the appearance of chronological and/or environmentally-caused skin aging.

15 Claims, No Drawings

(56) References Cited

U.S. PATENT DOCUMENTS

| | | |
|---|---|---|
| 2018/0280286 A1 | 10/2018 | Elsen-Wahrer et al. |
| 2019/0038689 A1 | 2/2019 | Kalahasti et al. |
| 2019/0151214 A1 | 5/2019 | Shaffer et al. |
| 2019/0192393 A1 | 6/2019 | Chen et al. |
| 2019/0290639 A1 | 9/2019 | Jackson |
| 2020/0121627 A1 | 4/2020 | Park |
| 2021/0228467 A1 | 7/2021 | Baek |

FOREIGN PATENT DOCUMENTS

| | | | | |
|---|---|---|---|---|
| CN | 109475472 A | 3/2009 | | |
| CN | 106580798 B | 8/2019 | | |
| CN | 110368326 A | 10/2019 | | |
| EP | 1742710 B1 | 6/2009 | | |
| JP | 2013-170124 A | 9/2013 | | |
| WO | WO 2005/070380 A1 | 8/2005 | | |
| WO | WO 2008/030308 A1 | 3/2008 | | |
| WO | WO-2012053009 A2 * | 4/2012 | ............... | A61K 8/06 |
| WO | WO 2016/141315 A1 | 9/2016 | | |
| WO | WO 2018/081779 A1 | 5/2018 | | |
| WO | WO 2020/081868 A1 | 4/2020 | | |
| WO | WO 2020/086820 A1 | 4/2020 | | |
| WO | WO 2021/212077 A3 | 6/2022 | | |

OTHER PUBLICATIONS

European Patent Office, Extended European Search Report, European Patent Application No. 19874453.4, Jun. 27, 2022, nine pages.

Kameyama, K. et al., "Inhibitory effect of magnesium l-ascorbyl-2-phosphate (VC-PMG) on melanogenesis in vitro and in vivo," Journal of the American Academy of Dermatology, vol. 34, Iss. 1, Jan. 1996, pp. 29-33.

Kim, S. et al., "Stabilization of L-ascorbic acid in cosmetic emulsions," Journal of Industrial and Engineering Chemistry, vol. 57, Jan. 25, 2018, pp. 193-198.

Maia, A.M. et al., "Validation of HPLC stability-indicating method for Vitamin C in semisolid pharmaceutical/cosmetic preparations with glutathione and sodium metabisulfite, as antioxidants," Talanta, vol. 71, Jun. 12, 2006, pp. 639-643.

PCT International Search Report and Written Opinion, PCT Application No. PCT/US2022/047305, Jan. 24, 2023, 18 pages.

PCT International Search Report and Written Opinion, PCT Application No. PCT/US2022/077119, Jan. 18, 2023, 19 pages.

PCT International Search Report and Written Opinion, PCT Application No. PCT/US2021/027835, Aug. 11, 2021, 17 pages.

PCT International Search Report and Written Opinion, PCT Application No. PCT/US2021/027834, Aug. 12, 2021, 14 pages.

PCT International Search Report and Written Opinion, PCT Application No. PCT/US2021/027832, May 11, 2022, 18 pages.

PCT International Search Report and Written Opinion, PCT Application No. PCT/US2021/027831, Aug. 11, 2021, 16 pages.

PCT International Search Report and Written Opinion, PCT Application No. PCT/US2021/027830, Aug. 11, 2021, 17 pages.

PCT International Preliminary Report on Patentability, PCT Application No. PCT/US2021/027830, Oct. 27, 2022, ten pages.

PCT International Search Report and Written Opinion, PCT Application No. PCT/US2021/027827, Jul. 16, 2021, 13 pages.

PCT International Preliminary Report on Patentability, PCT Application No. PCT/US2021/027827, Oct. 27, 2022, seven pages.

PCT International Search Report and Written Opinion, PCT/US2019/056822, dated Dec. 27, 2019, 16 pages.

Sarkar, R. et al., "Cosmeceuticals for Hyperpigmentation: What is Available?," Journal of Cutaneous and Aesthetic Surgery, vol. 6, No. 1, Jan. 2013, pp. 4-11.

Wikipedia, "Ferulic acid," Jan. 24, 2020, seven pages, [Online] Retrieved from the Internet <URL: https://en.wikipedia.org/w/index.php?title=Ferulic_acid&oldid=937396103>.

Ferreira, A.S. et al., "In Vivo Xylitol Primary Dermal Irritation and Phototoxicity Evaluation," Latin American Journal of Pharmacy, vol. 28, No. 2, Mar. 2009, pp. 192-195.

United States Office Action, U.S. Appl. No. 17/965,633, May 10, 2023, 16 pages.

United States Office Action, U.S. Appl. No. 17/286,434, May 4, 2023, 17 pages.

China National Intellectual Property Administration, Office Action w/English Translation, Chinese Patent Application No. 202180036744.7, Oct. 21, 2023, 16 pages.

* cited by examiner

HIGH-POTENCY VITAMIN C AND SUGAR ALCOHOL TOPICAL FORMULATIONS

This application is a continuation application of co-pending Patent Cooperation Treaty (PCT) International Application No. PCT/US2021/027827, filed Apr. 16, 2021, which claims the benefit of U.S. Provisional Application No. 63/010,884, filed Apr. 16, 2020, the disclosures of which are hereby incorporated by reference in their entirety.

FIELD OF INVENTION

Compositions and methods for treating, preventing, or improving dermatocosmetic conditions, including reducing the appearance of skin aging.

INTRODUCTION

Ascorbic acid (also commonly known as Vitamin C) is a potent antioxidant and is widely used in topical compositions to treat or prevent a range of cosmetic and/or dermatological conditions as well as to reduce the appearance of chronological and/or environmentally-caused skin aging, such as facial fine lines and wrinkles, dyschromia/uneven pigmentation, and dark circles under the eyes). Additionally, Vitamin C can help neutralize the damaging effects of free radicals and plays a role in stimulating the growth and bundling of collagen, important in maintaining skin elasticity.

Tyrosinase is a copper-containing enzyme that catalyzes the production of melanin and other pigments from tyrosine by oxidation. The antioxidant activity of ascorbic acid is reported to mediate, and thereby reduce (inhibit) the rate of melanogenesis. Y K Choi et al, Int J Dermatol. Vol. 49, pp. 218-26 (2010).

The "gold standard" in cosmetic dermatology for skin lightening/brightening is hydroquinone (HQ). However, HQ can have side effects including mild burning, stinging, erythema (redness), and skin dryness. Vitamin C is also used to lighten the appearance of the skin—including for example, dark circles under the eyes—but with a more favorable safety profile (i.e., fewer side effects). See, e.g., L E Espinal-Perez et al, Int J Dermatol. Vol. 43, pp. 604-7 (2004) (93% improvement from use of 4% HQ versus 62.5% improvement from use of 5% Vitamin C; but 68.7% side-effects from HQ versus 6.2% from Vitamin C).

The scientific and patent literature describe Vitamin C topical products, especially water-containing formulations, as "unstable".

Research and development activities seeking more stable topical Vitamin C formulations have focused on creating esterified derivatives (e.g., magnesium ascorbyl phosphate ("MAP") and ascorbyl-6-palmitate), using anhydrous carrier systems, adding antioxidants or other ingredients to Vitamin C formulations, and buffering Vitamin C formulations to a low pH.

The efficacy of Vitamin C formulations depends to a large extent on concentration. For example, a cream containing 10% MAP is reported to effectively brighten/lighten the appearance of the skin. See K Kameyama et al. *J Am. Acad. Dermatol*. Vol. 34, pp. 29-33 (1996). However, many skin care products contain vitamin C or a derivative at concentrations of less than 1%. R. Sarkar et al. *J Cutan Aesthet. Surg*. Vol. 6, No. 1, pp. 4-11 (2013).

Researchers in the Department of Chemical and Biomolecular Engineering, Yonsei University, Seoul, Republic of Korea investigated carrier-based approaches for reducing the oxidation of L-ascorbic acid in cosmetic emulsions. Emulsion stability (i.e., not separating into oil and water phases) as well as the effects of changes in the pH, color, and concentration of L-ascorbic acid were studied in four types of emulsions: water-in-oil (W/O), propylene glycol-in-oil (PG/O), butylene glycol-in-oil (B/O), and glycerine-in-oil (G/O) emulsions. The G/O emulsion that used glycerine as the dispersed phase retained the highest proportion of the initial L-ascorbic acid (LAA) content over time, followed by the PG/O, B/O, and W/O emulsions. Sehui Kim, Tai Gyu Lee "Stabilization of L-ascorbic acid in cosmetic emulsions" J Ind. Chem. Eng. Vol. 57, pp. 193-198 (2018).

In topical compositions, the use of urea (and substituted ureas) is known, including for moisture retention (as a humectant), for keratolytic activity, as well as for penetration enhancement, both for itself and other active ingredients. At concentrations of lower than about 10%, urea acts as a moisturizer. At higher concentrations, from about 10% up to 40%, urea can be used to treat dry/rough skin conditions, including ichthyosis and psoriasis.

It is also known in the art that inclusion of urea at efficacious concentrations in aqueous topical compositions poses formulating challenges. Urea undergoes steady hydrolysis, producing ammonia and other amines, compounds that not only have an unpleasant odor but also tend to increase pH. Moreover, hydrolysis of urea in aqueous compositions can cause discoloration or other breakdown of the, e.g., US Publication No. 2008/0175919.

There has been and remains a need for non-oily/non-greasy topical formulations that contain and maintain a high concentration of Vitamin C without degradation, and concomitant decrease in biological activity. These needs are met by the high-potency Vitamin C concentrates of the present disclosure.

SUMMARY

Topical formulations of L-ascorbic acid dissolved in a combination of a sugar alcohol agent, and a non-aqueous skin-compatible solvent are provided. The formulations are storage stable for an extended period of time without significant degradation of the L-ascorbic acid in the composition, and have desirable physical properties. The topical formulations can include high concentrations of the L-ascorbic acid of 10 to 28% by weight, and 5% to 20% by weight of a sugar alcohol agent. Topical compositions of this disclosure find use in treating or preventing a variety of cosmetic and/or dermatological conditions as well as to reduce the appearance of chronological and/or environmentally-caused skin aging.

DETAILED DESCRIPTION

This disclosure provides topical formulations of L-ascorbic acid dissolved in a combination of a sugar alcohol agent and a non-aqueous skin-compatible solvent. The formulations are storage stable for an extended period of time without undesirable discoloration or significant degradation of the L-ascorbic acid in the composition. This disclosure provides particular topical formulations which have been developed and optimized to provide skin compatibility and desirable physical properties.

Topical compositions of this disclosure find use in treating or preventing a variety of cosmetic and/or dermatological conditions as well as to reduce the appearance of chronological and/or environmentally-caused skin aging, such as facial fine lines and wrinkles, dyschromia or uneven pigmentation, dark circles under the eyes, and remove or reduce skin pathogens. Non-limiting examples of dermatocosmetic conditions that may be improved by topical application of the compositions of the present disclosure include: keratoses, melasma, lentigines, liver spots, inflammatory dermatoses (including eczema, acne, psoriasis), bacterial infection on the skin, and xeroses (also known in the art as dry skin or pruritus).

In some embodiments, formulations of the present disclosure include the ingredients: (i) 5 to 28% by weight ascorbic acid; and (ii) sugar alcohol agent dissolved in (iii) a non-aqueous skin-compatible solvent.

Ascorbic Acid

This disclosure provides formulations that include combination of particular amount of a sugar alcohol agent in a non-aqueous skin-compatible solvent which together can provide for dissolution of particular amounts of ascorbic acid and which produce skin-compatible liquid compositions in which the ascorbic acid is substantially stable to decomposition. In some embodiments, the amounts of ascorbic acid stably dissolved in the composition are greater than would otherwise be possible without the particular combinations of ingredients provided by this disclosure.

The terms "ascorbic acid", "L-ascorbic acid" and "vitamin C" are used interchangeably herein, and refer to the naturally occurring vitamin of CAS Registry Number: 50-81-7. Any convenient form of ascorbic acid can be utilized in the subject formulations. In some embodiments, the ascorbic acid used in the high potency Vitamin C concentrate of the present disclosure is a powder.

In certain embodiments, the ascorbic acid material used in preparing the subject compositions is composed of granular particles. Such a particulate powder has a particle size (e.g., mean particle size) of less than about 25 microns, such as less than about 20 microns, and more preferably less than about 12.5 microns, e.g., as measured by a Hagman gauge. In some embodiments, all of the ascorbic acid powder used in preparing the subject compositions is capable of passage through a No. 100 U.S. Standard Sieve, a standard testing procedure used by the US Pharmacopoeia. In some embodiments, 80% or more (such as 90% or more, or 100%) of ascorbic acid powder used in preparing the subject composition is capable of passage through a No. 325 U.S. Standard Sieve. For example, one powder meeting the above criterion is Ascorbic Acid Ultra-Fine Powder from DSM Nutritional Products LLC, Parsippany, NJ Previously, this product was available as Product Code No. 6045653 from Roche Vitamins and Fine Chemicals.

In some embodiments, the amount of ascorbic acid in the subject composition is at least about 5% by weight, such as at least about 10% by weight, at least about 12% by weight, at least about 15% by weight, at least about 20% by weight, or at least about 25% by weight. In some embodiments, the subject composition includes about 28% by weight or less of ascorbic acid in the non-aqueous solvent solution, such as about 25% by weight or less. In certain embodiments, the non-aqueous solvent is 1,3-propanediol. In particular embodiments, the amount of ascorbic acid in the subject composition is between about 10% by weight and about 20% by weight, or between about 12% by weight and about 28% by weight, such as between about 15% by weight and about 28% by weight, or between about 20% by weight and about 28% by weight. In some embodiments, the amount of ascorbic acid in the subject composition is about 5%, about 6%, about 7%, about 8%, about 9%, about 10%, about 11%, about 12%, about 13%, about 14%, about 16%, about 17%, about 18%, about 19%, about 20%, about 21%, about 22%, about 23%, about 24%, about 25%, about 26%, about 27%, about 28%, about 29%, or about 30% by weight.

In general, the amounts of ascorbic acid in a composition are calculated relative to the solution phase based on the non-aqueous solvent. See Formulations of Tables 1-3. However, the amounts of ascorbic acid and other ingredients relative to the emulsion composition as a whole can readily be calculated by the skilled artisan. Formulations of Tables 1-3 show exemplary emulsion compositions where the % by weight values shown are relative to the total emulsion composition. It is understood that, in some cases, these concentrate solutions having particular amounts of ascorbic acid can be combined with an immiscible ingredient (e.g., an oil component) and an emulsifying agent to produce an emulsion composition (e.g., as described below).

Sugar Alcohol Agent

The formulations of the present disclosure include a sugar alcohol agent in an amount sufficient to enhance the solubility of ascorbic acid in the non-aqueous skin compatible solvent and to provide a stable solution. The inventor discovered that particular amounts of sugar alcohol agent can be added to a non-aqueous solvent to increase the maximum amount of ascorbic acid that can be solubilized without recrystallization. Additionally, these formulations provide stable solutions of ascorbic acid at various desired concentration levels.

A sugar alcohol agent refers to a sugar alcohol or a sugar alcohol derivative, i.e., an agent that includes a sugar alcohol linked (e.g., via an ether linkage) to a saccharide via one of its alcohol groups. In some embodiments, the sugar alcohol is an acyclic C4-C6 polyalcohol compound, e.g., of formula $HOCH_2(CHOH)_n CH_2OH$, where n is 2-4. In some embodiments, the sugar alcohol agent includes a C4-C6 sugar alcohol, e.g., a C5-C6 sugar alcohol. In some embodiments, the sugar alcohol agent is a C4-C6 sugar alcohol, e.g., a C5-C6 sugar alcohol.

A sugar alcohol derivative refers to a compound that includes a sugar alcohol linked to a second moiety. In some embodiments, the sugar alcohol derivative includes a sugar alcohol linked (e.g., via an ether linkage) to a saccharide (e.g., a monosaccharide or disaccharide) via one of its alcohol groups. Sugar alcohol derivatives of interest include, but are not limited to, xylitylglucoside, anhydroxylitol, lactitol, and the like.

Sugar alcohol agents of interest include, but are not limited to, xylitol and xylitol derivatives such as xylitylglucoside and anhydroxylitol; sorbitol; lactitol; maltitol; erythritol; and mannitol. In certain embodiments, the sugar alcohol agent is xylitol. The sugar alcohol agent ingredient used in the subject formulations can be a combination of sugar alcohols. For example, the sugar alcohol agent can be a combination of xylitol and erythritol. Xylitol, in non-skincare industries, can be used for reducing or eliminating bacterial growth, such as *Staphylococcus*. For example, xylitol has been shown to prevent demineralization of teeth and bones, otitis media infection, respiratory tract infections, inflammation and cancer progression.

The culprits that effect microbiome growth on the skin include pH, moisture, pores, and nutrients such as sweat in the skin that promote bacterial growth. The present inventors found that xylitol can be used in the topical compositions of this disclosure for controlling the skin-microflora balance due to its selective effects and inhibition of pathogenic bacteria, such as *Staphylococcus aureus* found on the skin, while maintaining the integrity of healthy skin microflora such as *Staphylococcus epidermidis* (SE) that provides protection against the growth of pathogenic bacteria. Additionally, the combination of ascorbic acid and xylitol controls the pH and increases hydration of the skin, thereby reducing the amount of harmful pathogenic microbes present on the skin's surface.

In some embodiments, the percent by weight amount of sugar alcohol agent in the composition of the present disclosure is an amount that is sufficient to solubilize ascorbic acid in the non-aqueous solvent. In some embodiments, the amount of sugar alcohol agent in the compositions of this disclosure is defined as a function of the concentration of ascorbic acid ([AA]). For AA concentrations exceeding the maximum solubility of ascorbic acid in the neat non-aqueous solvent alone ([Xs]), as a first step, subtract [Xs] from the desired concentration of AA in the concentrate solution. Thus, ([Xs]) is the maximum concentration of ascorbic acid that can be dissolved in the neat non-aqueous solvent. As a second step, multiply the difference from the first step by (Y). The minimum amount (% wt) of a sugar alcohol agent (S) to be included in the non-aqueous solvent based compositions can be calculated by the formula:

$$([AA]-[Xs])*(Y).$$

In some embodiments, (Y) is 0.5±0.2. In some embodiments, (Y) is 1.0±0.5. In some embodiments, (Y) is 1.5±0.5. In some embodiments, (Y) is 2.0±0.5. In some embodiments, (Y) is 2.5±0.5. In some embodiments, (Y) is 3.0±0.5. In some embodiments, (Y) is 4.0±0.5. In some embodiments, (Y) is 4.5±0.5. In some embodiments, (Y) is 5.0±0.5. In some embodiments, (Y) is 5.5±0.5. In some embodiments, (Y) is 5.5±0.5. In some embodiments, (Y) is 6.0±0.5. In some embodiments, (Y) is 6.5±0.5. In some embodiments, (Y) is 7±0.5. In some embodiments, (Y) is 7.5±0.5. In some embodiments, (Y) is 8.0±0.5. In some embodiments, (Y) is 8.5±0.5. In some embodiments, (Y) is 9.0±0.5. In some embodiments, (Y) is 9.5±0.5. In some embodiments, (Y) is 10.0±0.5. In some embodiments, (Y) is 1.0 or more, such as 1.5 or more, 2.0 or more, 2.5 or more, 3.0 or more, 3.5 or more, 4.0 or more, 4.5 or more, 5.0 or more. 5.5 or more, 6.0 or more, 6.5 or more, 7.0 or more, 7.5 or more, 8.0 or more, 8.5 or more, 9.0 or more, 9.5 or more, or 10.0 or more.

In some embodiments, the sugar alcohol agent is dissolved at a concentration that is at least ([AA]−[Xs])*(1.25) or greater, where [AA] is the concentration of ascorbic acid (% wt) and [Xs] is the maximum solubility (% wt) of ascorbic acid in the neat non-aqueous solvent.

In some embodiments, the sugar alcohol agent is dissolved at a concentration that is at least ([AA]−[Xs])*(1.50) or greater, where [AA] is the concentration of ascorbic acid (% wt) and [Xs] is the maximum solubility (% wt) of ascorbic acid in the neat non-aqueous solvent.

In some embodiments, the amount of a sugar alcohol agent in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of a sugar alcohol agent in the non-aqueous solvent solution, such as about 25% by weight or less.

In certain embodiments, the non-aqueous solvent is 1,3-propanediol. In particular embodiments, the amount of a sugar alcohol agent in the subject composition is between about 10% by weight and about 20% by weight, or between about 12% by weight and about 28% by weight, such as between about 15% by weight and about 28% by weight, or between about 20% by weight and about 28% by weight. In some embodiments, the amount of a sugar alcohol agent in the subject composition is about 5%, about 10%, about 15%, about 20%, or about 25% by weight.

In some embodiments, the subject composition includes about 1 to 30% by weight of a sugar alcohol agent (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) and a non-aqueous solvent. In some embodiments, the subject composition includes between 5-10%, about 10-15%, or about 15-20% by weight of a sugar alcohol agent, and a non-aqueous solvent. In certain embodiments, the subject composition includes about 5% by weight of a sugar alcohol agent and a non-aqueous solvent. In certain embodiments, the subject composition includes about 15% by weight of a sugar alcohol agent and a non-aqueous solvent. In certain embodiments, the subject composition includes about 20% by weight of a sugar alcohol agent and a non-aqueous solvent.

In some embodiments, the subject composition includes about 5 to 7% by weight of a sugar alcohol agent and a non-aqueous solvent. In some embodiments, the subject composition includes about 7 to 9% by weight of a sugar alcohol agent and a non-aqueous solvent. In certain embodiments, the subject composition includes about 9 to 11% by weight of a sugar alcohol agent and a non-aqueous solvent. In certain embodiments, the subject composition includes about 11 to 13% by weight of a sugar alcohol agent and a non-aqueous solvent. In certain embodiments, the subject composition includes about 13 to 15% by weight of a sugar alcohol agent and a non-aqueous solvent. In certain embodiments, the subject composition includes about 15 to 17% by weight of a sugar alcohol agent and a non-aqueous solvent. In certain embodiments, the subject composition includes about 17 to 19% by weight of a sugar alcohol agent and a non-aqueous solvent. In certain embodiments, the subject composition includes about 19 to 21% by weight of a sugar alcohol agent and a non-aqueous solvent. In certain embodiments, the subject composition includes about 21 to 23% by weight of a sugar alcohol agent and a non-aqueous solvent. In certain embodiments, the subject composition includes about 23 to 25% by weight of a sugar alcohol agent and a non-aqueous solvent.

In some embodiments, the sugar alcohol is xylitylglucoside. In some embodiments, the amount of xylitylglucoside in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of xylitylglucoside in the non-aqueous solvent solution, such as about 25% by weight or less.

In some embodiments, the sugar alcohol is anhydroxylitol. In some embodiments, the amount of anhydroxylitol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of anhydroxylitol in the non-aqueous solvent solution, such as about 25% by weight or less.

In some embodiments, the sugar alcohol is sorbitol. In some embodiments, the amount of sorbitol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of sorbitol in the non-aqueous solvent solution, such as about 25% by weight or less.

In some embodiments, the sugar alcohol is lactitol. In some embodiments, the amount of lactitol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of lactitol in the non-aqueous solvent solution, such as about 25% by weight or less.

In some embodiments, the sugar alcohol is maltitol. In some embodiments, the amount of maltitol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of maltitol in the non-aqueous solvent solution, such as about 25% by weight or less.

In some embodiments, the sugar alcohol is erythritol. In some embodiments, the amount of erythritol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of erythritol in the non-aqueous solvent solution, such as about 25% by weight or less.

In some embodiments, the sugar alcohol is mannitol. In some embodiments, the amount of mannitol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of mannitol in the non-aqueous solvent solution, such as about 25% by weight or less.

In some embodiments, the sugar alcohol is a combination of xylitol and erythritol. In some embodiments, the amount of the combination of xylitol and erythritol in the subject composition is at least about 5% by weight, such as at least about 6% by weight, at least about 7% by weight, at least about 8% by weight, at least about 9% by weight, at least about 10% by weight, at least about 11% by weight, at least about 12% by weight, at least about 14% by weight, at least about 15% by weight, at least about 16% by weight, at least about 17% by weight, at least about 18% by weight, at least about 19% by weight, at least about 20% by weight, at least about 21% by weight, at least about 22% by weight, at least about 23% by weight, at least about 24% by weight, or at least about 25% by weight. In some embodiments, the subject composition includes about 28% by weight or less of the combination of xylitol and erythritol in the non-aqueous solvent solution, such as about 25% by weight or less.

Skin Compatible Solvent

In addition to the sugar alcohol agent and cinnamic acid (e.g., as described herein), the high-potency Vitamin C formulations of the present disclosure contain, as an essential ingredient, at least one non-aqueous skin-compatible solvent. A skin compatible solvent is a non-aqueous solvent that does not cause irritation or sensitization when applied topically to the skin. Non-aqueous skin-compatible solvents of interest include polyols, C(1-6) alkanediols, glycol ethers, dimethyl ethers, and combinations thereof.

In some embodiments, the solvent is a skin compatible polyol. A polyol is an organic alcohol solvent having two or more hydroxy groups. In some embodiments, the polyol solvent is a C(3-6)polyol. In some embodiments, the polyol solvent is a polyether polyol. In some embodiments, the polyol solvent is a polyester polyol. Skin compatible polyols of interest include, but are not limited to, glycerol (1,2,3-propanetriol); diglycerol; propylene glycol (1,2-propanediol); dipropylene glycol; 1,3-propanediol; butylene glycol (1,3-butanediol); 1,2-butanediol; pentylene glycol (1,2-pentanediol); 1,5-pentanediol; 1,2-hexanediol; 1,6-hexanediol; 1,2,3-hexanetriol, 1,2,6-hexanetriol; ethoxydiglycol; and dimethyl isosorbide. In some embodiments, the solvent is a glycol ether, a dimethyl ether, or a combination thereof. A preferred skin-compatible solvent is 1,3-propanediol, commercially available from DuPont Tate & Lyle BioProducts LLC under the tradename ZEMEA®. In some embodiments, the solvent is a mixture of 1,3 propanediol and 1,2 hexanediol.

In some embodiments, the subject composition includes about 10 to 99% by weight (e.g. about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, or about 99% or more) of a non-aqueous skin compatible solvent. In some embodiments, the subject composition includes about 1 to 30% by weight of an agent (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) and 10 to 99% polyol. In some embodiments, the subject composition includes about 1 to 30% by weight of an agent (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) and 10 to 99% polyol and one or more additional skin compatible solvents.

Additional Components

A formulation may contain one or more (optional) additional ingredients. Any convenient ingredient known to the skilled artisan to provide cosmetic/aesthetic benefits can be utilized in the subject formulations. Such cosmetic/aesthetic benefits include, but are not limited to, reducing the appearance of fine lines/wrinkles, improving skin barrier function (by reducing the rate/extent of trans-epidermal water loss), making the skin feel smoother/more supple/softer, creating the appearance of more even skin tone (reducing dyschromia) and/or "glow"/radiance (also described in the art as "brightness").

In some embodiments, the composition further includes one or more optional additional components (e.g., as described herein). In some embodiments, the one or more optional additional components are selected from tocopherols, tocotrienols (e.g., alpha, beta, delta and gamma tocopherols or alpha, beta, delta and gamma tocotrienols), azelaic acid, hydroxy acids (e.g., salicylic acid), urea agents (e.g. urea, hydroxyethyl urea), panthenol, *Pinus pinaster* bark extract, emulsifying agent, hyaluronic acid complex, madecassoside, madecassoside asiaticoside, acetyl zingerone, bakuchiol, and bis-ethylhexyl hydroxydimethoxy benzylmalonate.

Each optional additional component (e.g., as described herein) may be present in an amount of 10% or less by weight of the composition, such as 9% or less, 8% or less, 7% or less, 6% or less, 5% or less, 4% or less, 3% or less, 2% or less, 1% or less by weight. In some embodiments the total amount of the one or more optional additional components (e.g., as described herein) in the composition 10% or less by weight, such as 9% or less, 8% or less, 7% or less, 6% or less, 5% or less, 4% or less, 3% or less, 2% or less, 1% or less by weight.

In some embodiments, the urea agent may be present in an amount of 20% or less, 15% or less, 10% or less, 5% or less, 4% or less, 2% or less, or 1% or less by weight. In certain embodiments, the urea agent is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% by weight.

In some embodiments, the composition further includes 10% or less by weight in total of one or more optional additional components selected from an antioxidant, a skin lightening agent, and a moisturizing agent.

Cinnamic Acid

In some embodiments, the formulations of the present disclosure also include a cinnamic acid and sources thereof, which are known to work synergistically with ascorbic acid to provide additional antioxidant protection to skin. Cinnamic acids of interest and sources thereof include, but are not limited to, ferulic acid, caffeic acid and coumaric acid. In some embodiments, the cinnamic acid is ferulic acid. The cinnamic acid ingredient used in the subject formulation can be a combination of ferulic acid and/or substituted cinnamic acids. For example, the cinnamic acid can be a combination of ferulic acid and caffeic acid.

In some embodiments, the subject composition includes about 0.1% to 2% by weight of the cinnamic acid (e.g., about 0.1%, about 0.5%, about 1%, about 1.5%, or about 2%).

The formulations of the present disclosure include cinnamic acid and derivatives thereof (e.g., ferulic acid, caffeic acid, coumaric acid, sinapinic acid, and other phenolic cinnamic acids), cis and trans isomers thereof, salts thereof, equivalents thereof.

In some embodiments, the composition of the present disclosure includes 0.1% or more by weight of cinnamic acid or derivatives thereof. In some embodiments, the composition includes 0.1% to 5.0% by weight of cinnamic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of cinnamic acid or derivatives thereof. In some embodiments, the composition includes about 0.1 to 5.0% by weight of cinnamic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of cinnamic acid or derivatives thereof).

Suitable cinnamic acids or derivatives thereof that can be used in the composition of the present disclosure are found in U.S. Pat. No. 6,596,761, the disclosure of which is hereby incorporated by reference in its entirety.

The term "derivatives of caffeic acid, coumaric acid, ferulic acid" is to be understood as meaning their cosmetically or pharmacologically acceptable esters, salts and base adducts, in particular those such as are described above for the cinnamic acid derivatives.

Ferulic Acid and Derivatives Thereof

In some embodiments, the cinnamic acid derivative is a ferulic acid. Ferulic acid is an antioxidant that increases AA's photoprotective effect on skin. It can also stabilize AA in aqueous systems. In some embodiments, the composition of the present disclosure includes ferulic acid or derivatives thereof. In some embodiments, the ferulic acid is E-ferulic acid. In some embodiments, the ferulic acid is Z-ferulic acid. In some embodiments, the ferulic acid is a mixture of E- and Z-ferulic acid.

Ferulic acid, when combined with Vitamin C and/or Vitamin A, can protect vitamin A and vitamin C thereby improving the photoprotective action of these vitamins. In combination with vitamin C, ferulic acid can provide two to four times as much photoprotection against ultraviolet radiation thus helping to minimize the harmful effects (e.g., erythema or formation of sunburn cells) caused by ultraviolet radiation. Ferulic acid can also improve the chemical stability of vitamin C and/or vitamin E to enhance a synergistic and longer lasting photoprotective effect.

In some embodiments, ferulic acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of ferulic acid by enhancing skin penetration.

In some embodiments, the composition of the present disclosure includes 0.1% or more by weight of ferulic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of ferulic acid or derivatives thereof. In some embodiments, the composition includes about 0.1 to 5.0% by weight of ferulic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of ferulic acid or derivatives thereof).

In certain embodiments, the composition includes 2% or less by weight of the ferulic acid, such as 1.5% or less, 1.0% or less (e.g., about 1% by weight), or 0.5% or less (e.g., about 0.5% by weight) of the ferulic acid.

In some embodiments, ferulic acid (e.g., 4-hydroxy-3-methoxy-cinnamic acid, caffeic acid 3-methyl ether) is characterized by the structural formula

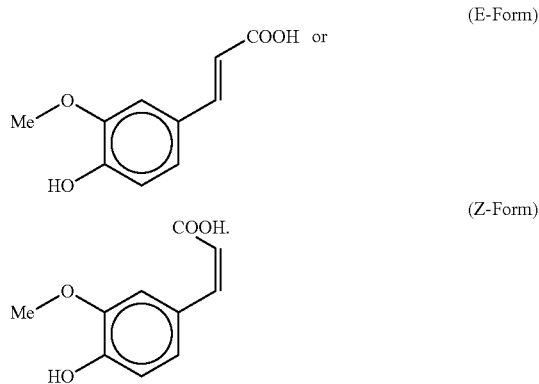

Caffeic Acid and Derivatives Thereof

In some embodiments, the cinnamic acid derivative is a caffeic acid. Caffeic acid is an antioxidant that increases AA's photoprotective effect on skin. It can also stabilize AA in aqueous systems. In some embodiments, the composition of the present disclosure includes caffeic acid or derivatives thereof.

In some embodiments, caffeic acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of caffeic acid by enhancing skin penetration.

In some embodiments, the composition of the present disclosure includes 0.1% or more
by weight of caffeic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of caffeic acid or derivatives thereof. In some embodiments, the composition includes about 0.1 to 5.0% by weight of caffeic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of caffeic acid or derivatives thereof).

In some embodiments, caffeic acid comprises the structure:

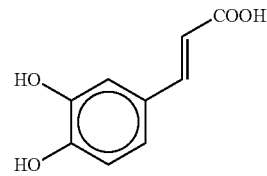

In some embodiments, the cinnamic acid derivative is a combination of ferulic acid and caffeic acid. In some embodiments, the cinnamic acid derivative is trans-ferulic acid and caffeic acid.

Coumaric Acid and Derivatives Thereof

In some embodiments, the cinnamic acid derivative is a coumaric acid. Coumaric acid is an antioxidant that increases AA's photoprotective effect on skin. It can also stabilize AA in aqueous systems. In some embodiments, the composition of the present disclosure includes coumaric acid or derivatives thereof. In some embodiments, coumaric acid comprises p-coumaric acid.

In some embodiments, coumaric acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of coumaric acid by enhancing skin penetration.

In some embodiments, the composition of the present disclosure includes 0.1% or more by weight of coumaric acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of coumaric acid or derivatives thereof. In some embodiments, the composition includes about 0.1 to 5.0% by weight of coumaric acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of coumaric acid or derivatives thereof).

Sinapinic Acid (e.g., Hydroxycinnamic Acids) and Derivatives Thereof

In some embodiments, the cinnamic acid derivative is sinapinic acid or derivatives thereof. Sinapinic acid is an antioxidant that increases AA's photoprotective effect on skin. It can also stabilize AA in aqueous systems. In some embodiments, the composition of the present disclosure includes sinapinic acid or derivatives thereof.

In some embodiments, sinapinic acid or derivatives thereof is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of sinapinic acid or derivatives thereof by enhancing skin penetration.

In some embodiments, the composition of the present disclosure includes 0.1% or more by weight of sinapinic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of sinapinic acid or derivatives thereof. In some embodiments, the composition includes about 0.1 to 5.0% by weight of sinapinic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of sinapinic acid or derivatives thereof).

In some embodiments, the sinapinic acid includes the general formula:

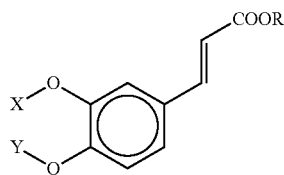

and/or active amounts of cinnamic acid derivatives of the formula:

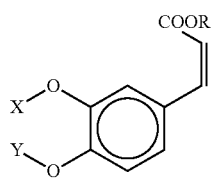

wherein the groups X, Y an R independently of one another can be chosen from the group consisting of H and branched and unbranched alkyl having 1-18 C atoms, for example 1-6 C atoms, can be used.

Tocopherol or Tocotrienol Agent

In some embodiments, the composition further includes optional additional component that is a tocopherol or tocotrienol agent. In some embodiments, the tocopherol or tocotrienol agent is a form of Vitamin E selected from alpha, beta, delta and gamma tocopherols and alpha, beta, delta and gamma tocotrienols, and combinations thereof. In some embodiments, the tocopherol or tocotrienol is alpha-tocopherol.

In some embodiments, the tocopherol or tocotrienol agent is present in the composition in an amount of 2% or less by weight, such as 1.5% or less, 1% or less, or 0.5% or less by weight.

In some embodiments of any one of the formulations described herein, the formulation excludes tocopherol or tocotrienol agents, e.g., or precursors thereof having vitamin E activity. In certain embodiments of any one of the formulations described herein, the formulation excludes vitamin E acetate.

Antioxidants

In certain embodiments, the formulation contains a secondary antioxidant (i.e., in addition to Vitamin C or the optional additive tocopherol or tocotrienol agent).

Preferred secondary antioxidants include, terpenoid antioxidants, and benzoic acid derivatives (e.g., p-hydroxy benzoic acid, gallic acid, or protocatechuic acid). In some embodiments, the secondary antioxidant is *Pinus pinaster* bark extract. In some embodiments, the secondary antioxidant is zingerone or acetyl zingerone. In some embodiments, the secondary antioxidant is bakuchiol (10309-37-2) a natural terpenoid antioxidant. In some embodiments, the secondary antioxidant is bis-ethylhexyl hydroxydimethoxy benzylmalonate (HDBM).

The secondary antioxidant, when included, is preferably present in an amount in the range of 0.1 to 3%, more preferably 0.1 to 2% by weight of the composition, such as 0.1 to 1% by weight, 0.1 to 0.5% by weight, e.g., about 0.2%, about 0.3%, about 0.4% or about 0.5% by weight. In some embodiments, the secondary antioxidant is acetyl zingerone.

Skin Lightening Agents

In certain embodiments, the formulation contains a secondary skin lightening agent (e.g., as defined herein) (i.e., in addition to Vitamin C). Skin lightening agents which may be included in compositions of the present disclosure include, but are not limited to: hydroquinone and its derivatives, including, for example, its monomethyl and monobenzyl ethers; licorice root (*Glycyrrhiza glabra*) extract; azelaic acid; kojic acid; arbutin; retinoids (including all-trans-retinoic acid, adapalene and tazarotene); alpha hydroxy acids, in particular citric acid, lactic acid, and glycolic acid; ellagic acid; gluconic acid; gentisic acid (2,5-dihydrobenzoic acid); 4-hydroxy benzoic acid; salts and esters of the above-mentioned acids, including ammonium lactate and sodium lactate; N-acetyl glucosamine; aloesin, a hydroxymethyl chromone isolated from aloe vera; Vitamin B3 compound or its derivative—niacin, nicotinic acid, niacinamide. Epigallocatechin 3-O-gallate (EGCG), and other catechin constituents of tea extracts, in particular green tea; extract of soybean oil (*Glycine soja*), including isoflavones; hydroxystilbene; butyl hydroxy anisole; and butyl hydroxy toluene may also be utilized as a skin lightening agent. In some embodiments, the additional skin lightening agent is azelaic acid or arbutin.

The skin lightening agent, when included, is preferably present in an amount in the range of 0.1 to 10%, more preferably 0.2 to 5% by weight of the composition, such as 0.2 to 4% by weight, 0.2 to 3% by weight, or 0.2 to 2% by weight. In certain embodiments, the secondary skin lightening agent is soluble and may be added directly to the high Vitamin C (>15%) concentrate of the present invention. The secondary skin lightening agent may also be encapsulated using techniques known to the person having ordinary skill in the art.

Hydroxy Acids

In some embodiments, formulation contains a hydroxy acid, e.g., a small molecule compound including a carboxylic acid and a hydroxy group. The acid may be an alkyl carboxylic acid or a benzoic acid. The hydroxy group can be a phenol or an alkyl alcohol. In certain embodiments, the hydroxy acid is an alpha-hydroxy carboxylic acid. In certain embodiments the hydroxy acid contains 2-12 carbon atoms, such as 2-6 or 2-4 carbons. Hydroxy acids of interest include, but are not limited to, glycolic acid, lactic acid, mandelic acid, salicylic acid, capryloyl salicylic acid, salicyloyl phytosphingosine, gluconolactone, lactobionic acid, maltobionic acid, and combinations thereof.

Anti-Inflammatory

In some embodiments, formulation contains an anti-inflammatory agent as an additional ingredient. In some embodiments, the anti-inflammatory agent is madecassoside, madecassoside asiaticoside, or madecassic acid. The anti-inflammatory agent, when included, is preferably present in an amount in the range of 0.1 to 2%, more preferably 0.1 to 1% by weight of the composition, such as 0.1 to 0.5% by weight, or 0.1 to 0.2% by weight. In some embodiments, madecassoside or madecassoside asiaticoside, is included in an amount in the range of 0.1 to 0.5%, such as about 0.1% or about 0.2% by weight.

Emulsion Compositions

It is understood that any of the non-aqueous liquid compositions having particular amounts of ascorbic acid (e.g., as described herein) can be combined with an immiscible phase or ingredient (e.g., an oilcomponent) to produce an emulsion composition. In some embodiments, the non-aqueous liquid composition that makes up the first phase of an emulsion composition is referred to as a concentrate. The liquid concentrate can be mixed with one or more additional components (e.g., an immiscible oil phase or component and an optional emulsifying agent) to produce an emulsion. A variety of methods and ingredients for preparing emulsions are available and can be used in the subject emulsion compositions.

In some embodiments, an emulsion composition of this disclosure is referred to as a gel.

Any convenient oils and lipids can be utilized in the oil component of the subject emulsions. An oil component or oil phase refers to any phase that is immiscible with the non-aqueous liquid composition. In some embodiments, the oil component is silicone-based, e.g., includes a silicone polymer. In some embodiments, the oil component includes a silicone oil or silicone elastomer, such as a polyorganosiloxane. In some embodiments, the silicone polymers have dual characteristics, and can be used as emulsifiers and/or act as the continuous/dispersed phase of the emulsion composition.

Oils and lipids of interest include, but are not limited to, silicone oils, linseed oil, tsubaki oil, macadamia nut oil, corn oil, mink oil, olive oil, avocado oil, sasanqua oil, castor oil, safflower oil, apricot oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, teaseed oil, evening primrose oil, eggyoke oil, neetsfoot oil, liver oil, triglycerine, glycerine trioctanate, pentaerythritol tetraoctanate, glycerine triisopalmitate, cholesterol, free fatty acids, and combinations thereof.

Any convenient emulsifying agents or emulsifiers can be utilized in the preparation of the subject emulsions to stabilize the composition and prevent separation of the oil component from the solvent solution (e.g., the non-aqueous liquid composition). Exemplary emulsifying agents include but are not limited to polysorbates, laureth-4, potassium cetyl sulfate, and silicone and silicone-elastomer-based emulsifiers and emulsifying blends. In some embodiment, a surfactant such as a monoglyceride, sorbitan fatty acid ester, or polyglycerine fatty acid ester, polyoxyethylene hardened castor oil, polyoxyethylene fatty acid ether, is added thereto in a small amount, and the stability is further improved.

Storage Stability

In general, the high-potency Vitamin C and sugar alcohol formulations of the present disclosure are storage stable. Storage stability can refer to the lack of chemical or physical degradation of any component(s) of interest in a composition. Storage stability can refer to a lack of physical degradation of a liquid formulation over time, e.g., lack of precipitation, crystallization or separation of one or more components of a liquid formulation into a separate phase. Such precipitation, crystallization or separation can reduce the concentration or amount of the component in the liquid composition. Storage stability can refer to a lack of chemical degradation of a component of a formulation over time, e.g., where chemical degradation can refer to hydrolysis of a component susceptible to hydrolysis, or oxidation or reduction of a component susceptible to such a redox reaction. A lack of degradation can mean less than a 10% change in the amount of the component in the composition, such as less than 5%, less than 4%, less than 3%, less than 2%, or less than 1% change over the period of time of interest (e.g., a storage time as described herein).

In some embodiments, storage stability refers to maintaining the ascorbic acid content of the formulation over time. High-potency Vitamin C and sugar alcohol formulations of the present disclosure are capable of maintaining at least 90%, at least 95%, at least 96%, at least 97%, at least 98%, at least 99% of the starting ascorbic acid content when the concentrate is stored at room temperature for 1 month or longer, 2 months or longer, 3 months or longer, 4 months or longer, 5 months or longer, 6 months or longer, 7 months or longer, 8 months or longer, 9 months or longer, 10 months or longer, 11 months or longer, 12 months or longer, 13 months or longer, 14 months or longer, 15 months or longer, or 16 months or longer.

The amount of ascorbic acid content in a composition can be determined using a wide range of techniques including, but not limited to: titrimetric, spectrophotometric, electrochemical, fluorimetric, enzymatic and chromatographic. Methods for determining ascorbic acid content in a topical formulation can be complicated/confounded by the presence of excipients or other antioxidant agents (e.g., agents for stabilizing Vitamin C), as well as degradation products. Of the above-listed methods, high performance liquid chromatography is preferred. See, A M Maia et al., "Validation of HPLC stability-indicating method for Vitamin C in semi-solid pharmaceutical/cosmetic preparations . . . " Talanta Vol. 71, pp. 639-643 (2007).

In some embodiments, the storage stable composition of this disclosure demonstrates less than 10 mol % degradation of the ascorbic acid after storage for 1 weeks or longer, 2 weeks or longer, 3 weeks or longer, 4 weeks or longer, 5 weeks or longer, 6 weeks or longer (e.g., 8 weeks or longer, 10 weeks or longer, 12 weeks or longer, 16 weeks or longer, 18 weeks or longer, 24 weeks or longer, or even longer) at 40° C.±2° C. in a sealed (e.g., air tight sealed environment for containing the composition, and separation from the atmosphere) container, such as less than 9 mol %, less than 8 mol %, less than 7 mol %, less than 6 mol %, less than 5 mol %, less than 4 mol %, less than 3 mol %, less than 2 mol %, or less than 1% degradation of the ascorbic acid initially present in the composition prior to storage.

In some embodiments, the storage stable composition of this disclosure demonstrates less than 10 mol % degradation of the ascorbic acid after storage for 4 weeks or longer (e.g., 6 weeks or longer, 8 weeks or longer, 10 weeks or longer, 12 weeks or longer, 16 weeks or longer, 18 weeks or longer, 24 weeks or longer, or even longer) at 45° C.±2° C. in a sealed container, such as less than 9 mol %, less than 8 mol %, less than 7 mol %, less than 6 mol %, less than 5 mol %, less than 4 mol %, less than 3 mol %, less than 2 mol % degradation of the ascorbic acid initially present in the composition prior to storage.

In some embodiments, the storage stable composition of this disclosure demonstrates less than 10 mol % degradation of the ascorbic acid after storage for 6 months or longer (e.g., 8 months or longer, 10 months or longer, 12 months or longer, 18 months or longer, or even longer) at 25° C.±2° C. in a sealed container or a multi-use container, such as less than 9 mol %, less than 8 mol %, less than 7 mol %, less than 6 mol %, less than 5 mol %, less than 4 mol %, less than 3 mol %, less than 2 mol % degradation of the ascorbic acid initially present in the composition prior to storage. In certain embodiments, the composition is stored in a sealed container. In certain embodiments, the composition is stored in a multi-use container.

In some embodiments, the storage stable composition of this disclosure demonstrates less than 20 mol % degradation of the ascorbic acid after storage for 12 months or longer (e.g., 18 months or longer, 24 months or longer, or even longer) at 25° C.±2° C. in a sealed container or a multi-use container, such as less than 15 mol %, less than 12 mol %, less than 10 mol %, less than 8 mol %, less than 6 mol %, less than 6 mol %, less than 4 mol %, less than 3 mol %, less than 2 mol % degradation of the ascorbic acid initially present in the composition prior to storage. In certain embodiments, the composition is stored in a sealed container. In certain embodiments, the composition is stored in a multi-use container.

Containers

In some embodiments, the high potency Vitamin C concentrate of the disclosure is administered with a second non-aqueous formulation (i.e., oil, ester and/or silicone carrier). The two compositions can be pre-filled into a "dual-chamber" container—a pump container in which two formulations are stored separately prior to dispense—with a high-potency Vitamin C concentrate of the invention in a first chamber, and a non-aqueous formulation in a second chamber. Some dual-chamber containers have two separate actuators/pumps, each having an orifice for dispensing one of the two formulations. Other dual-chamber containers contain two pumps and one actuator from which the two formulations are dispensed—either side-by-side (e.g., through two orifices), or from a single shared orifice. A non-limiting example of a dual-chamber container is described in U.S. Pat. No. 6,462,025.

Any containers suitable for storing and/or dispensing the subject formulations can be adapted for use. The container can provide an air tight sealed environment for containing the composition, and separation from the atmosphere. The container can prevent during storage undesirable degradation, e.g., from absorption of light and/or moisture from the atmosphere or surrounding environment. Provided are ready-to-use topical preparations of ascorbic acid in a multi-use container which is pre-filled with a storage stable topical composition (e.g., as described herein).

Additional packaging for the container can be included. In some cases, the packaging provides a further barrier that prevents absorption of light and/or moisture from the atmosphere or surrounding environment.

Methods of Preparation

Also provided by this disclosure are processes for stabilizing ascorbic acid for storage that include preparation of any one of the subject formulations (e.g., as described herein), e.g., by dissolving ascorbic acid in a non-aqueous solvent with a sugar alcohol agent and one or more optionally additional components to provide a stable liquid composition capable of storage stability.

In some embodiments, the process includes combining:
1. 1% to 20% by weight a sugar alcohol agent selected from xylitol and xylitol derivatives such as xylitylglucoside and anhydroxylitol; sorbitol; lactitol; maltitol; erythritol; mannitol, and combinations thereof;
2. 10% to 94% by weight of a non-aqueous skin-compatible solvent comprising $C_{(3-6)}$polyol, ethoxydiglycol, dimethyl ether, or a combination thereof; and
3. optionally one or more additional agents; with
4. 5% to 28% by weight ascorbic acid;
thereby dissolving the ascorbic acid to produce storage stable, nonaqueous, single-phase clear liquid composition of ascorbic acid. In certain embodiments, the one or more additional agents are combined and include: 0.5% to 2% ferulic acid; and 0.5% to 2% *Pinus pinaster* bark extract. In certain embodiments, the one or more additional agents are combined and include: 3% to 10% by weight azelaic acid.

In some embodiments, the process further includes: combining 0.5% to 2% by weight of Vitamin E and 1.5% to 5% by weight of an emulsifying agent to produce a second liquid composition; and combining the second liquid composition with the liquid composition of ascorbic acid to produce an emulsion. In some embodiments, the process further includes: combining 0.5% to 2% by weight of a lipid component and 1.5% to 5% by weight of an emulsifying agent to produce a second liquid composition; and combining the second liquid composition with the liquid composition of ascorbic acid to produce an emulsion.

In some embodiments of the process, the one or more additional agents are combined and include: 0.5% to 2% by weight hydroxy acid. In certain embodiments, the hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof. In some embodiments of the process, the one or more additional agents are combined and include: 0.1% to 5% by weight hydroxy acid. In certain embodiments, the hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof.

Also provided are product storage stable formulations produced by the process according to any one of the embodiments described herein.

Definitions

The following definitions are set forth to illustrate and define the meaning and scope of the terms used in the description.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

"At least one" means one or more, and also includes individual components as well as mixtures/combinations.

Numbers used in describing quantities of ingredients and/or reaction conditions are to be understood as being modified in all instances by the term "about." Unless otherwise indicated, percentages and ratios are to be understood as based upon the total weight of the concentrate.

Numerical ranges are meant to include numbers within the recited range, and combinations of subranges between the given ranges. For example, a range from 1-5 includes 1, 2, 3, 4 and 5, as well as subranges such as 2-5, 3-5, 2-3, 2-4, 1-4, etc.

The terms "formulation" and "composition" are used interchangeably herein.

It is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are described herein.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed. All patents and publications referred to herein are expressly incorporated by reference.

ADDITIONAL EMBODIMENTS

Additional Embodiments of this disclosure are described in the following aspects.

Aspect 1. A storage stable topical liquid composition comprising:
5% to 28% by weight ascorbic acid;
5% to 20% by weight of a sugar alcohol agent; and
less than 10% by weight in total of one or more optional additional components;
dissolved in a non-aqueous skin-compatible solvent comprising polyol, C(1-6) alkanediol, glycol ether, dimethyl ether, or a combination thereof.

Aspect 2. The composition of aspect 1, wherein the composition demonstrates less than 3 mol % degradation of the ascorbic acid after storage for 8 weeks at 40° C.±2° C. in a sealed container.

Aspect 3. The composition of aspect 1, wherein the composition demonstrates less than 3 mol % degradation of the ascorbic acid after storage for 8 months at 40° C.±2° C. in a multi-use container.

Aspect 4. The composition of aspect 1, wherein the composition demonstrates less than 5 mol % degradation of the ascorbic acid after storage for 16 months at 40° C.±2° C. in a multi-use container.

Aspect 5. The composition of any one of aspects 1-4, wherein the sugar alcohol agent is selected from xylitol and xylitol derivatives.

Aspect 6. The composition of any one of aspects 1-5, wherein the sugar alcohol agent is selected from xylitylglucoside, anhydroxylitol, sorbitol, lactitol, maltitol, erythritol, mannitol, and combinations thereof.

Aspect 7. The composition of any one of aspects 1-4, wherein the sugar alcohol agent is a C5-C6 sugar alcohol.

Aspect 8. The composition of aspect 7, wherein the sugar alcohol agent is xylitol.

Aspect 9. The composition of aspect 8, wherein the composition comprises 7-20% by weight of xylitol.

Aspect 10. The composition of aspect 9, wherein the composition comprises 7-15% by weight of xylitol.

Aspect 11. The composition of aspect 10, wherein the composition comprises 10-15% by weight of xylitol.

Aspect 12. The composition of aspect 10, wherein the composition comprises 7-10% by weight of xylitol.

Aspect 13. The composition of any one of aspects 8 to 12, wherein the composition comprises 10-20% by weight of ascorbic acid.

Aspect 14. The composition of any one of aspects 8 to 12, wherein the composition comprises 15-20% by weight of ascorbic acid.

Aspect 15. The composition of any one of aspects 8 to 12, wherein the composition comprises 15% by weight of ascorbic acid.

Aspect 16. The composition of any one of aspects 1-15, wherein the solvent is selected from 1,3 propanediol, 1,2 propanediol, 1,3 butanediol, 1,5 pentanediol, 1,2 hexanediol, 1,6 hexanediol, glycerol, diglycerol, ethoxydiglycol, and dimethyl isosorbide.

Aspect 17. The composition of any one of aspects 1-16, wherein the solvent is 1,3 propanediol.

Aspect 18. The composition of any one of aspects 1-16, wherein the solvent is a mixture of 1,3 propanediol and 1,2 hexanediol.

Aspect 19. The composition of any one of aspects 1-18, wherein the composition comprises the one or more additional components.

Aspect 20. The composition of aspect 19, wherein the one or more additional components comprise a chemical exfoliant (e.g., at 0.1 to 2% in the composition).

Aspect 21. The composition of aspect 20, wherein the chemical exfoliant is salicylic acid.

Aspect 22. The composition of any one of aspects 19-21, wherein the one or more additional components comprise a moisturizing agent (e.g., at 1 to 5% in the composition).

Aspect 23. The composition of aspect 22, wherein the moisturizing agent is a urea agent or glycerin.

Aspect 24. The composition of aspect 19, wherein the one or more additional components are selected from tocopherols, tocotrienols (e.g., alpha, beta, delta and gamma tocopherols or alpha, beta, delta and gamma tocotrienols), azelaic acid, hydroxy acids (e.g., salicylic acid), a urea agent, panthenol, *Pinus pinaster* bark extract, ferulic acid, glycerin, emulsifying agent, hyaluronic acid complex, madecassoside, madecassoside asiaticoside, acetyl zingerone, bakuchiol, and bis-ethylhexylhydroxydimethoxybenzylmalonate.

Aspect 25. The composition of aspect 19, wherein the one or more optional additional components are selected from one or more of: salicylic acid, ferulic acid, *Pinus pinaster* bark extract, urea agent and glycerin.

Aspect 26. The composition of any one of aspects 19-25, wherein the composition comprises 0.5% salicylic acid.

Aspect 27. The composition of any one of aspects 19-25, wherein the composition comprises 0.5% ferulic acid.

Aspect 28. The composition of aspect 27, wherein the composition comprises 0.5% salicylic acid and 0.5% ferulic acid.

Aspect 29. The composition of any one of aspects 19-25, wherein the composition comprises 1.5% ferulic acid.

Aspect 30. The composition of any one of aspects 19-30, wherein the composition comprises 0.5% *Pinus pinaster* bark extract.

Aspect 31. The composition of any one of aspects 19-30, wherein the one or more additional component comprises a urea agent.

Aspect 32. The composition of aspect 31, wherein the urea agent is selected from urea, hydroxyethyl urea, or a combination of urea and hydroxyethyl urea.

Aspect 33. The composition of aspect 32, wherein the composition comprises 2.5% urea.

Aspect 34. The composition of aspect 33, wherein the composition comprises 2.5% urea, 0.5% salicylic acid, and 0.5% ferulic acid.

Aspect 35. The composition of any one of aspects 1-34, wherein the ascorbic acid is dissolved at a concentration that is above its maximum concentration in the solvent alone.

Aspect 36. The composition of any one of aspects 1-19, wherein the composition comprises:
15% to 20% by weight ascorbic acid;
7% to 10% by weight of xylitol; and
less than 10% by weight in total of one or more optional additional components selected from urea, salicylic acid, and ferulic acid;
dissolved in 1,3 propanediol or 1,2 propanediol.

Aspect 37. The composition of aspect 36, wherein the composition comprises 15% by weight of ascorbic acid.

Aspect 38. The composition of any one of aspects 36 to 37, wherein the composition comprises 7.5% by weight of xylitol.

Aspect 39. The composition of any one of aspects 36 to 38, wherein the composition comprises 2.5% urea.

Aspect 40. The composition of any one of aspects 36 to 39, wherein the composition comprises 0.5% salicylic acid.

Aspect 41. The composition of any one of aspects 36 to 40, wherein the composition comprises 0.5% ferulic acid.

Aspect 42. The composition of aspect 1, wherein the composition is of Table 2.

Aspect 43. The composition of aspect 1, wherein the composition is of Table 3.

Aspect 44. The composition of any one of aspects 1-43, wherein the xylitol-containing composition, when applied to skin, reduces or eliminates pathogenic *staphylococcus* mutants while maintaining the integrity of *Staphylococcus epidermis*.

Aspect 45. A ready-to-use topical preparation in a multi-use container which is pre-filled with a storage stable topical composition according to any one of aspects 1-43, wherein the multi-use container comprises means for dispensing a single dose of the storage stale topical composition.

Aspect 46. The preparation of aspect 45, wherein the storage stale topical composition demonstrates less than 3 mol % degradation of the ascorbic acid after storage for 4 weeks at 40° C.±2° C. in the container.

Aspect 47. The preparation of aspect 45, wherein the storage stable topical composition demonstrates less than 3 mol % degradation of the ascorbic acid after storage for 8 months at 40° C.±2° C. in the container.

Aspect 48. The preparation of aspect 45, wherein the storage stable topical composition demonstrates less than 5 mol % degradation of the ascorbic acid after storage for 16 months at 40° C.±2° C. in the container.

Aspect 49. The preparation of any one of aspects 45-48, wherein the storage stable topical composition is sealed from the atmosphere in the container.

Aspect 50. The preparation of any one of aspects 45-49, wherein the container is placed in packaging.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The invention is further defined by reference to the following examples. These examples are representative, and should not be construed to limit the scope of the invention.

EXAMPLES

Example 1: Assessment of Formulation Components

A series of experiments were performed to assess and optimize the components of the subject formulations. AA refers to L-ascorbic acid. S refers to sugar alcohol agent. % values are wt %.

Summary of Experiments:
Ascorbic Acid (AA) and Sugar Alcohol (S) Dissolved in Non-Aqueous Solvent The maximum amount of AA solubilized in 1,3-propanediol before recrystallization was ~12%. This solubility limit was also observed for propylene glycol (1,2 propanediol). We discovered that mixtures of ascorbic acid and a sugar alcohol such as xylitol could be dissolved in non-aqueous solvent such as 1,3-propanediol to provide for stable solution. Use of a combination of ascorbic acid and xylitol also provided for stable solutions having high concentrations of AA, e.g., at a concentrations higher than what could be achieved in the solvent alone.

Solvents 1,3 propanediol, 1,2 propanediol, butylene glycol, pentylene glycol, and hexanediol were identified as preferred solvents. 1,3 propanediol (trade name: Zemea) is inherently different from and preferable to the various polyols described. Below is a review of various polyols and reasons why 1,3 propanediol is unique and preferable:

- 1,3-propanediol, sometimes referred to in the art as propanediol, is unique in that it possesses a combination of gentleness on skin (even applied neat, or at 100% concentration), relatively low viscosity (and therefore perceived "lightness" on skin), environmental friendliness (not petroleum-derived), natural derivation (corn or sugar cane), low odor, and moderate ability to solubilize ascorbic acid.
- 1,2-propanediol, otherwise referred to in the art as propylene glycol, although of low viscosity and possessing a moderate ability to solubilize ascorbic acid, is well-known for inducing skin irritation and sensitivity. Additionally, it is derived from petroleum and possesses an unpleasant odor, reminiscent of acetone.
- 1,3-butanediol, otherwise referred to in the art as butylene glycol, is of low viscosity, possesses a moderate ability to solubilize ascorbic acid, and is relatively gentle on skin. However, like propylene glycol, it is derived from petroleum (not environmentally friendly) and possesses an unpleasant odor, reminiscent of acetone.
- also applicable to dipropylene glycol
- 1,5-pentanediol, otherwise referred to in the art as pentylene glycol, possesses a moderate ability to solubilize ascorbic acid, low odor, and certain versions are not derived from petroleum but from sugarcane or corn. However, upon application to skin, it imparts a "heavier", less desirable texture on skin. Additionally, its recommended use level is capped at 5%, limiting usage as a primary solvent.
- 1,2-hexanediol possesses a moderate ability to solubilize ascorbic acid. However, upon application to skin, it imparts a "heavier", less desirable texture on skin, possesses an unpleasant odor reminiscent of acetone, and is derived from petroleum. Additionally, its recommended use level is capped at 10%, limiting usage as a primary solvent.
- Glycerin and diglycerin, possess a moderate ability to solubilize ascorbic acid, are relatively gentle on skin, are low-odor, and are not derived from petroleum. However, they are of a very viscous nature, and impart not only an undesirable, "heavy" texture on skin, but one that is exceedingly sticky.
- Dimethyl isosorbide is relatively gentle on skin and not derived from petroleum, and imparts a "light", not undesirable texture when applied to skin. However, it has a very limited ability to solubilize ascorbic acid and possesses a slight, but noticeable chemical odor reminiscent of chlorine.

Optional Additional Components

Additional ingredients were chosen for their compatibility with (e.g., miscibility in) 1,3 propanediol, 1,2 propanediol, and 1,3 butanediol. Additional notes and observations on each optional additional component are shown below.

Panthenol (Pro-Vitamin B5)

This is a humectant that shows soothing and moisturizing properties for skin. Both enantiomers, D-panthenol and L-panthenol, are potent humectants. However, only D-panthenol is converted into pantothenic acid in the skin, which confers additional benefits to skin (wound healing, for example).

Research shows that it can reduce irritation to skin by other ingredients

Research also shows barrier-repairing ability (stimulation of physiologic lipid synthesis)

DL-panthenol is a racemic mixture of the two enantiomers; it is in powdered/crystal form.

D-panthenol is a viscous liquid.

DL-panthenol is freely soluble in 1,3 propanediol, 1,2 propanediol and 1,3 propanediol (up to 50%)

D-panthenol is also freely soluble in 1,3 propanediol, 1,2 propanediol and 1,3 propanediol, with no risk of recrystallization at any concentration (as it is already liquid at room temperature).

Inhibition of transepidermal water loss is apparent at concentrations of 1% and above.

Hyaluronic Acid

Hyaluronic acid is a humectant that shows the ability to form a viscoelastic film on skin that prevents transepidermal water loss.

It is usually incorporated in aqueous solutions in its salt form, sodium hyaluronate However, there is a raw material blend that is largely free from water, in which it is incorporated in a vehicle of glyceryl polymethacrylate, butylene glycol (1,3 butanediol), and natto gum (trade name Hydrafilm 3MW by The Innovation Company). This makes it compatible with the non-aqueous formulations of the present disclosure.

Documents from The Innovation Company show usage of this material up to 9.1% by weight of the final formula.

The chemical composition is as follows:

75-85% glyceryl polymethacrylate 15-20% butylene glycol 0.5-2% natto gum 0.5-2% hyaluronic acid

*Pinus pinaster* Bark Extract

Components of the bark extract of *Pinus pinaster* species show the ability to recycle vitamin C.

Additionally, there is research to show their general antioxidant, anti-inflammatory and anti-acne properties.

pycnogenol may be used as an alternative when *Pinus pinaster* bark extract is desired, a material blend from Kinetik called Pantrofina Skin360 (PS360) is utilized in the subject formulations.

PS360, unlike pycnogenol, is already in liquid form as it uses diglycerin as a solvent, making it very easy to incorporate.

Additionally, Res Pharma Industriale provides in-vitro and clinical data to show effectiveness against free radical damage, inflammation and acne at a concentration of 0.5% by weight of PS360.

The chemical composition is as follows:

90-95% diglycerin 5-10% *Pinus pinaster* bark extract

Madecassoside

*Centella asiatica* extract is often used for its soothing properties.

Madecassoside is a highly purified glycosylated triterpene of *Centella asiatica*. It is sold by raw material supplier SEPPIC, who share in-vitro and clinical data showing its anti-inflammatory and other effects on skin.

This is a very expensive ingredient ($6.10 per gram), but clinical data from SEPPIC shows desirable ability to reduce erythema (skin redness) in concentrations of 0.2%.

At a concentration of 0.2%, madecassoside is soluble in 1,3 propanediol, 1,2 propanediol and 1,3 butanediol.

In some embodiments, madecassoside is madecassoside asiaticoside.

Azelaic Acid

Azelaic acid (AzA) is well studied for its ability to treat acne, rosacea and melasma, due to the fact that it was studied and sold as a prescription drug. Though poorly understood, these effects are believed to be a result of AzA's anti-bacterial, anti-inflammatory, and keratolytic effects, as well as its unique ability to cause apoptosis in abnormal melanocytes.

It is very poorly soluble in most solvents. As a result, all products currently on the market, both prescription and cosmetic, are sold as opaque emulsions, where the AzA is not solubilized but instead finely milled into a powder and suspended in the viscous vehicle.

Because of an inability to solubilize AzA, a preferred component for maximizing delivery into the skin of active ingredients, the team behind prescription product Finacea (currently considered to be the gold standard) chose to manipulate pH, as they discovered that, counterintuitively, a salt form of AzA (formed in aqueous environments in which the pH is higher than the pKa of AzA, 4.15), is slightly better at penetrating skin.

I've discovered that AzA can be solubilized in 1,3 propanediol at relatively high concentrations—up to 10%.

The solubility of AzA in 1,3 propanediol can be slightly increased by the presence of hydroxyethyl urea.

For example, it is possible to solubilize 7.5% AzA with 10% AA, 5% U in a 1,3 propanediol base.

Acetyl Zingerone

Acetyl zingerone is a broad-spectrum antioxidant that can prevent lipid peroxidation. It was engineered to be a more stable, more potent derivative of zingerone.

Sytheon provides in-vitro and clinical data showing its antioxidant, photoprotective, and anti-aging properties Acetyl zingerone may be used as a replacement for tocopherol.

Acetyl zingerone is readily soluble in 1,3 propanediol, 1,2 propanediol and 1,3 butanediol at the desired concentrations (0.5-1%), eliminating the need for emulsifiers as would be required for tocopherol Glycyrrhizic Acid Glycyrrhizic acid, like many other derivatives from licorice root (*Glycyrrhiza glabra, Glycyrrhiza uralensis*), shows anti-inflammatory, antioxidant and skin lightening properties.

Unlike 18B-glycyrrhetinic acid, glycyrrhizic acid shows solubility in 1,3-propanediol.

other derivatives of licorice root can be use, such as dipotassium glycyrrhizate, monoammonium glycyrrhizate, etc.

Example 2: Exemplary Formulations

The exemplary formulations of Tables 1-3 were prepared and assessed.

TABLE 1

Exemplary Formulations 1-3

| Formulation | 1,3-Propanediol | Xylitol | L-Ascorbic Acid |
|---|---|---|---|
| 1 | 77.5% | 7.5% | 15% |
| 2 | 80 | 7.5 | 12.5 |
| 3 | 85 | 5 | 12 |

TABLE 2

Components of Exemplary Compositions (% by weight)

| | Formulation | | | | | | | | | |
|---|---|---|---|---|---|---|---|---|---|---|
| | 1 | 2 | 3 | 4 | 5 | 6 | 7 | 8 | 9 | 10 |
| Ascorbic acid | 15% | 15% | 15% | 12% | 10% | 15% | 15% | 15% | 15% | 20% |
| C3-C6 polyol | 76.5% 1,3 pro-panediol | 74% 1,3 pro-panediol | 74.5% 1,3 pro-panediol | 78% 1,3 pro-panediol | 77.5% 1,3 pro-panediol | | 77.5% 1,3 pro-panediol | 77% 1,3 pro-panediol | 76.5% 1,3 pro-panediol | 63.5% 1,3 pro-panediol |
| Sugar Alcohol agent | 7.5% Xylitol | 7.5% Xylitol | 7.5% Xylitol | 5% Xylitol | 10% Xylitol | 7.5% | 7.5% Xylitol | 7.5% Xylitol | 7.5% Xylitol | 7.5% Xylitol |
| Ferulic acid | 0.5% | 0.5% | 0.5% | 0.5% | 0.5% | | | | | |
| Pinus Pinaster bark extract | 0.5% | 0.5% | 0.5% | 0.5% | 0.5% | | | | 0.5% | |
| Chemical Exfoliant | | 0.5% Salicylic acid | | | | 0.5% Salicylic acid | | | | |
| Moisturizing agent | | 2.5% Urea | 2.5% Urea | 2% Glycerin | 2% Glycerin | | | | | 9% Urea |
| Ferulic Acid | | | | | | | | 0.5% | | |

TABLE 3

Example Formulation

| Component | Percent by weight (%) |
|---|---|
| Propanediol | 74 |
| Xylitol | 7.5 |
| Urea | 2.5 |
| Salicylic Acid | 0.5 |
| Ferulic Acid | 0.5 |
| Ascorbic Acid | 15 |

The process of making the compositions as described in Tables 1-3 is described below.
1. The process of making the compositions include dispersing Xylitol, and Urea when present, into Zemea (Propanediol). The solution is then heated, then mixed until dissolved and solution is transparent.
2. The process then includes dispersing Salicylic Acid and Ferulic Acid. The solution is then mixed until dissolved and solution is transparent.
4. Next, the process includes dispersing Ascorbic Acid, mixed until dissolved and solution is transparent.

Example 3: Storage Stability Studies

Stability Method

Samples are stored in sealed containers, sealed from the atmosphere, at 40 degrees Celsius for up to 16 weeks. Results at 0 to 8 weeks are shown in Table 4. In general, 8 weeks storage under these conditions is expected to be equivalent to storage for 16 months at room temperature. The compositions in the containers are sampled at each time point, and assessed for levels of degradation of vitamin C using HPLC analysis.

Compositions

Exemplary compositions were prepared containing various percentages of Ascorbic Acid as shown in Tables 1-3.

The storage stability of these compositions was compared to control compositions that included the same amount of vitamin C dissolved in water with the addition of a ferulic acid in a concentration of 0.5%, tocopherol in a concentration of 1%, with additional components of a glycol ether, alkanediol, laureth-23, panthenol, triethanolamine, phenoxyethanol, and sodium hyaluronate. The results are shown in Table 4. The exemplary serum (approx. 15% vitamin C) compositions are still within specification after weeks 8 of testing (or the equivalent to 16 weeks at room temperature), as opposed to the control compositions which fell out of specification (OOS) by week 2 of testing (or equivalent to 4 months at room temperature).

TABLE 4

Storage stability

| Storage time | | % vitamin C by HPLC | |
|---|---|---|---|
| Week 40 degrees Celsius | Equiv. Months RT | Serum | Serum Control |
| 0 | 0 | 100.67% | 99.2% |
| 1 | 2 | 99.07% | 91.60% |
| 2 | 4 | 97.27% | *85.87% |
| 4 | 8 | 97.07% | *81.73% |
| 8 | 16 | 95.93% | *79.27% |

*indicates the samples were assessed as being OOS according to Out of Specification (OOS) Standards: 90% or less vitamin C stability.

The exemplary formulations of Tables 1-3 with approximately 15% Vitamin C were prepared and assessed as having desirable properties including storage stability.

What is claimed is:

1. A storage stable topical liquid composition comprising:
   a. 10% to 20% by weight ascorbic acid;
   b. 5% to 10% by weight of xylitol; and
   c. less than 10% by weight in total of one or more optional additional components;
   d. dissolved in a non-aqueous skin-compatible solvent selected from the group consisting of 1,3 propanediol, 1,2 propanediol, 1,3 butanediol, 1,5 pentanediol, 1,2 hexanediol, 1,6 hexanediol, glycerol, and a combination thereof,
   wherein the composition demonstrates less than 5 mol % degradation of the ascorbic acid after storage for 8 weeks at 40±2° C. in a sealed container.

2. The composition of claim 1, wherein the composition comprises 7 to 10% by weight of xylitol.

3. The composition of claim 1, wherein the composition comprises 15% by weight of ascorbic acid.

4. The composition of claim 1, wherein the solvent is 1,3 propanediol, or a mixture of 1,3 propanediol and 1,2 hexanediol.

5. The composition of claim 1, wherein the composition comprises the one or more additional components.

6. The composition of claim 1, wherein the ascorbic acid is dissolved at a concentration that is above its maximum concentration in the solvent alone.

7. The composition of claim 1, wherein the composition comprises:
   e. 15% to 20% by weight ascorbic acid;
   f. 7% to 10% by weight of xylitol; and
   g. less than 10% by weight in total of one or more optional additional components;
   h. dissolved in 1,3 propanediol, 1,2 propanediol, or a mixture of 1,3 propanediol and 1,2 hexanediol.

8. The composition of claim 7, wherein the composition comprises 15% by weight of ascorbic acid.

9. The composition of claim 7, wherein the composition comprises 7.5% by weight of xylitol.

10. The composition of claim 7, wherein the composition, when applied to skin, reduces or eliminates pathogenic *staphylococcus* mutants while maintaining the integrity of *Staphylococcus epidermis*.

11. A ready-to-use topical preparation in a multi-use container which is pre-filled with a storage stable topical composition of claim 1.

12. The composition of claim 1, wherein the composition comprises:
   a. 10% by weight ascorbic acid;
   b. 5% by weight of xylitol; and
   c. less than 10% by weight in total of one or more optional additional components;
   d. wherein the solvent comprises 1,3 propanediol and 1,2-hexanediol.

13. A storage stable topical liquid composition consisting of:
   a. 10% to 20% by weight ascorbic acid;
   b. 5% to 10% by weight of xylitol; and
   c. less than 10% by weight in total of one or more optional additional components;
   d. dissolved in a mixture of 1,3-propanediol and 1,2-hexanediol, wherein the composition comprises 2.5% or less of urea.

14. The composition of claim 13, wherein:
   the ascorbic acid is 15% to 20% by weight of the composition; and
   the xylitol is 7% to 10% by weight of the composition.

15. The composition of claim 13, wherein:
   the ascorbic acid is 10% by weight of the composition; and
   the xylitol is 5% by weight of the composition.

* * * * *